(12) United States Patent
Wagner et al.

(10) Patent No.: US 6,846,655 B1
(45) Date of Patent: Jan. 25, 2005

(54) METHODS FOR GENERATING HIGHLY DIVERSE LIBRARIES

(75) Inventors: Richard W. Wagner, Concord, MA (US); Martin C. Wright, Cambridge, MA (US); Brent Kreider, Bedford, MA (US)

(73) Assignee: Phylos, Inc., Lexington, MA (US)

( * ) Notice: Subject to any disclaimer, the term of this patent is extended or adjusted under 35 U.S.C. 154(b) by 0 days.

(21) Appl. No.: 09/434,834

(22) Filed: Nov. 5, 1999

Related U.S. Application Data (63) Continuation-in-part of application No. 09/342,980, filed on Jun. 29, 1999, now abandoned.
(60) Provisional application No. 60/090,970, filed on Jun. 29, 1998.

(51) Int. Cl.[7] .......................... C12P 19/34; C12Q 1/68; G01N 33/00; C07H 21/02; C07H 21/04
(52) U.S. Cl. .................... 435/91.2; 435/6; 435/91.1; 436/94; 536/23.1; 536/24.3; 536/24.33
(58) Field of Search ...................... 435/5, 6, 91.1, 435/91.2, 91.51, 91.32, 183; 436/94, 501; 536/23.1, 24.3, 24.33, 25.3

(56) References Cited

U.S. PATENT DOCUMENTS

| | | | |
|---|---|---|---|
| 4,994,379 A | | 2/1991 | Chang ........................ 435/69.1 |
| 5,447,839 A | | 9/1995 | Manos et al. ................... 435/5 |
| 5,525,715 A | * | 6/1996 | Racaniello et al. ....... 536/23.72 |
| 5,580,730 A | | 12/1996 | Okamoto ........................ 435/6 |
| 5,605,793 A | | 2/1997 | Stemmer ........................ 435/6 |
| 5,733,731 A | | 3/1998 | Schatz et al. .................... 435/6 |
| 5,733,743 A | | 3/1998 | Johnson et al. ............. 435/69.1 |
| 5,795,747 A | | 8/1998 | Henco et al. .............. 435/91.1 |
| 5,811,238 A | | 9/1998 | Stemmer et al. ................ 435/6 |
| 5,830,721 A | | 11/1998 | Stemmer et al. ......... 435/172.1 |
| 5,837,458 A | | 11/1998 | Minshull et al. ................ 435/6 |
| 5,912,119 A | * | 6/1999 | Radman et al. ................. 435/6 |
| 5,922,539 A | * | 7/1999 | Modrich et al. ............... 435/6 |
| 5,965,408 A | | 10/1999 | Short ........................ 435/91.1 |
| 6,015,660 A | * | 1/2000 | Lipkin et al. ................... 435/6 |
| 6,319,713 B1 | | 11/2001 | Patten et al. |

FOREIGN PATENT DOCUMENTS

| | | |
|---|---|---|
| EP | 0 774 511 A1 | 5/1997 |
| EP | 0 844 306 A1 | 5/1998 |
| WO | WO 92/18645 | 10/1992 |
| WO | WO 94/13804 | 6/1994 |
| WO | WO 97/08320 | 3/1997 |
| WO | WO 98/16636 | 4/1998 |
| WO | WO 98/41622 | 9/1998 |
| WO | WO 98/41623 | 9/1998 |
| WO | WO 98/58080 | 12/1998 |

OTHER PUBLICATIONS

Carninci et al., High–efficiency Full–length cDNA cloning by biotinylated CAP trapper. Genpmics 37, 327–336, 1996.*

(List continued on next page.)

*Primary Examiner*—Ethan Whisenant
*Assistant Examiner*—Frank Lu
(74) *Attorney, Agent, or Firm*—Clark & Elbing LLP (57) ABSTRACT

Disclosed herein is a method for generating a nucleic acid library, the method involving: (a) providing a population of single-stranded nucleic acid templates, each of the templates including a coding sequence and an operably linked promoter sequence; (b) hybridizing to the population of single-stranded nucleic acid templates a mixture of substantially complementary single-stranded nucleic acid fragments, the fragments being shorter in length than the nucleic acid template; (c) contacting each of the hybridization products of step (b) with both a DNA polymerase which lacks strand displacement activity and a DNA ligase under conditions in which the fragments act as primers for the completion of a second nucleic acid strand which is substantially complementary to the nucleic acid template; and (d) contacting the products of step (c) with RNA polymerase to generate an RNA library, the library being transcribed from the second nucleic acid strand.

55 Claims, 7 Drawing Sheets

OTHER PUBLICATIONS

Eberwine et al., Analysis of gene expression in single live neurons. Proc. Natl. Acad. Sci. USA, 89, 3010–3014, 1992.*

Van Gelder et al., Amplified RNA synthesized from limited quantities of heterogenous cDNA. Proc. Natl. Acad. Sci. USA, 87, 1663–1667, Mar. 1990.*

Gubler et al., A simple and very efficient method for generating cDNA libraries. Gene, 25, 263–269, 1983.*

Fishel et al., Gene conversion in *Escherichia Coli* resolution of heteroallellic mismatched nucleotide by co–repair. J. Mol. Biol., 188, 147–157, 1986.*

Sambrook et al., Molecular Cloning: A Laboratory Manual 2$^{nd}$ Ed (1989) Cold Spring Harbour Laboratory Press; Chapter 4; Single–Stranded, Filamentous Bacteriophage Vectors.

Alting–Mees et al., "pBluescript II: Gene Mapping Vectors," *Nucleic Acids Research* 17:9494 (1989).

Eggerding et al., "Construction of a Cloned Library of Adenovirus DNA Fragments in Bacteriophage M13," *J. Biol. Chem.* 258:10090–10097 (1983).

Jespers et al., "ζZLG6: A Phage Lambda Vector for High Efficiency Cloning and Surface Expression of cDNA Libraries on Filamentous Phage," *Gene* 173:179–181 (1996).

Rubenstein et al., "Subtractive Hybridization System Using Single–Stranded Phagemids with Directional Inserts," *Nucleic Acids Research* 18:4833–4842 (1990).

Swaroop et al., "Charon BS(+) and (–), Versatile λ Phage Vectors for Constructing Directional cDNA Libraries and Their Efficient Transfer to Plasmids," *Nucleic Acids Research* 16:8739 (1988).

Abelson, "Directed Evolution of Nucleic Acids by Independent Replication and Selection," *Science* 249:488–489 (1990).

Alberts, et al., "Recombinant DNA Technology," *Molecular Biology of The Cell*, Third Edition, 7:291–312 (1994).

Bishop et al., "Repair of Heteroduplex Plasmid DNA after Transformation into *Saccharomyces cerevisiae*," *Molecular and Cellular Biology* 6:3401–3409 (1986).

Botstein et al., "Strategies and Applications of in Vitro Mutagenesis," *Science* 229:1193–1201 (1985).

Campbell et al., "Single–Stranded DNA Gaps, Tails and Loops are Repaired in *Escherichia coli*," *Mutation Research* 211:181–188 (1989).

Clackson et al., "In Vitro Selection from Protein and Peptide Libraries," *Tibtech* 12:173–184 (1994).

Devlin et al., "Random Peptide Libraries; A Source of Specific Protein Binding Molecules," *Science* 249:404–406 (1990).

Eigen et al., "Molecular Quasi–Species," *Journal of Physical Chemistry* 92:6881–6891 (1988).

Eigen, "New Concepts for Dealing with the Evolution of Nucleic Acids," *Cold Spring Harb. Symp. Quant. Biol.* 52:307–320 (1987).

Eigen et al., "Evolutionary Molecular Engineering Based on RNA Replication," *Pure & Appl. Chem.* 56:967–978 (1984).

Fishel et al., "Gene Conversion in *Escherichia coli* Resolution of Heteroallelic Mismatched Nucleotides by Co–Repair," *J. Mol. Biol.* 188:147–157 (1986).

Fortini et al., "Different DNA Polymerases Are Involved in the Short– and Long–Patch Base Excision Repair in Mammalian Cells," *Biochemistry* 37:3575–3580 (1998).

Hanes et al. "In vitro Selection and Evolution of Functional Proteins by Using Ribosome Display," *Proc. Natl. Acad. Sci. USA* 94:4937–4942 (1997).

Higuchi, "Using PCR to Engineer DNA," *Stockton Press* pp. 61–70 (1989).

Horwitz et al., "Selection of New Biological Activities from Random Nucleotide Sequences: Evolutionary and Practical Considerations," *Genome* 31:112–117 (1989).

Hughes et al., "*Escherichia coli* DNA Polymerase II Is Stimulated by DNA Polymerase III Holoenzyme Auxilliary Subunits," *The Journal of Biological Chemistry* 266:4568–4573 (1991).

Irvine et al., "Systematic Evolution of Ligands by Exponential Enrichment with Integrated Optimization by Non–Linear Analysis," *J. Mol. Biol.* 222:739–761 (1991).

Jaiswal et al., "Efficient in vitro Repair of 7–Hydro–8–Oxodeoxyguanosine by Human Cell Extracts: Involvement of Multiple Pathways," *Nucleic Acids Research* 26:2184–2191 (1998).

Joyce et al., "A Novel Technique for the Rapid Preparation of Mutant RNAs," *Nucleic Acid Research* 17:711–722 (1989).

Kaczorowski, et al., "Co–operativity of Hexamer Ligation," *Gene* 179:189–193 (1996).

Leung et al., "A Method for Random Mutagenesis of a Defined DNA Segment Using a Modified Polymerase Chain Reaction," *Technique* 1:11–15 (1989).

Mattteucci et al., "Targeted Random Mutagenesis: The Use of Ambiguously Synthesized Oligonucleotides to Mutagenize Sequences Immediately 5' of an ATG Initiation Condon," *Nucleic Acids Research* 11:3113–3121 (1983).

Matthews et al., "Substrate Phage: Selection of Protease Substrates by Monovalent Phage Display," *Science* 260:1113–1117 (1983).

Mathews, et al., "Information Copying: Replication," *Biochemistry* pp. 826, 827, 122–127 and 902–909 (1990).

McCafferty et al., "Phage Antibodies: Filamentous Phage Displaying Antibody Variable Domains," *Nature* 348:552–554 (1990).

Mintz, et al., "EHD1–An EH Domain–Containing Protein with a Specific Expression Pattern," *Genomics* 59:66–71 (1999).

Nemoto et al., "In Vitro Virus: Bonding of mRNA Bearing Puromycin at the 3'–Terminal End to the C–Terminal End of its Encoded Protein on the Ribosome in vitro," *FEBS* 414:405–408 (1997).

Roberts and Szostak, "RNA–Peptide Fusions for the in Vitro Selection of Peptides and Proteins," *Proc. Natl. Acad. Sci. USA* 94:12297–12302 (1997).

Roberts, "In Vitro Selection of Proteins via RNA–Proteins Fusions," FY95, Abstract.

Roberts, "In Vitro Selection of Proteins via RNA–Proteins Fusions," FY96 Abstract.

Scott et al., Searching for Peptide Ligands with an Epitope Library, *Science* 249:386–390 (1990).

Stemmer, "Rapid Evolution of a Protein in vitro by DNA Shuffling," *Nature* 370:389–391 (1994).

Wagner et al., "Antisense Gene Inhibition by Oligonucleotides Containing C–5 Propyne Pyrimidines," *Science* 260:1510–1513 (1993).

Wells et al., "Cassette Mutagenesis: An Efficient Method for Generation of Multiple Mutations at Defined Sites," *Gene* 34:315–323 (1985).

Westmoreland et al., "Highly Mismatched Molecules Resemblimg Recombination Intermediates Efficiently Transform Mismtach Repair Proficient *Escherichia coli*," *Genetics* 145:29–38 (1997).

* cited by examiner

1. Single Strand DNA Production:

A. Normal PCR with one *phosporylated primer*

B. Digestion with *λ exonuclease (Roche)*

2. Fragment Preparation:

A. DNAase I digestion *in the presence of Mn2+*

Reasonably uniform fragments (~50-100 bps)

B. Purification with Centri-Sep Column (Princeton Separations). No Gel-purification 3. Extension and Ligation on Template

A. Basepairing of fragments to the template:

B. Extension with *Taq Stoffel Fragment (PE)*
Polymerase: NO Strand Displacement
NO 3'-5' Nuclease
NO 5'-3' Nuclease C. Sealing with *Ampligase (Epicentre):*

4. Amplification of Recombinant Strand

Fig.3

1. Single Strand DNA Production:
   A. Transcription with T7 RNA polymerase, followed by DNase I digestion to remove DNA templates B. Reverse transcription with reverse transcriptase, followed by RNase H digestion to remove mRNA templates. Pure, single-stranded DNA is produced.

2. Fragment Preparation:
   A. DNAase I digestion *in the presence of Mn2+*

Reasonably uniform fragments (~50-100 bp)

B. Purification with <u>Centri-Sep Column</u> (Princeton Separations). No Gel-purification 3. Extension and Ligation on Template
   A. Basepairing of fragments to the template:

B. Extension with *Taq Stoffel Fragment (PE)*
   Polymerase: NO Strand Displacement
   NO 3'-5' Nuclease
   NO 5'-3' Nuclease C. Sealing with *Ampligase (Epicentre)*:

Fig. 4-1

4. Amplification of Recombinant Strand

A. The recombinant strand can be specifically transcribed with a different RNA polymerase (such as SP6 polymerase), generating the corresponding mRNA ← SP6 Promoter B. The mRNA can then be converted by RT-PCR into double-strained DNA that corresponds to the recombinant strand

4. Amplification of Recombinant Strand

The recombinant strand can be specifically amplified with two primers that anneal to regions in the recombinant strand that are not present in the template DNA.

Fig. 5-2

METHODS FOR GENERATING HIGHLY DIVERSE LIBRARIES

CROSS REFERENCE TO RELATED APPLICATIONS

This application claims benefit from provisional application, Wagner, U.S. Ser. No. 60/090,970, filed on Jun. 29, 1998, now abandoned, and Wagner et al., U.S. Ser. No. 09/342,980, filed Jun. 29, 1999 now abandoned.

BACKGROUND OF THE INVENTION

In general, this invention relates to methods for generating and altering recombinant libraries.

The ability to isolate a desired nucleic acid or amino acid sequence requires the availability of recombinant libraries of sufficient number and diversity that a particular species is represented in the library and can be identified by one or more screening techniques. Such libraries facilitate the isolation of useful compounds, including therapeutics, research diagnostics, and agricultural reagents, as well as their coding sequences.

Moreover, desirable libraries may be specifically designed to contain large numbers of possible variants of a single compound. This type of library may be used to screen for improved versions of the compound, for example, for a compound variant having optimized therapeutic efficacy.

For these or any other application, general approaches for increasing library diversity are very useful and represent an important focus of the protein design industry.

SUMMARY OF THE INVENTION

In general, the present invention features a method for generating a nucleic acid library, the method involving: (a) providing a population of single-stranded nucleic acid templates, each of the templates including a coding sequence and an operably linked promoter sequence; (b) hybridizing to the population of single-stranded nucleic acid templates a mixture of substantially complementary single-stranded nucleic acid fragments, the fragments being shorter in length than the nucleic acid template; (c) contacting each of the hybridization products of step (b) with both a DNA polymerase which lacks strand displacement activity and a DNA ligase under conditions in which the fragments act as primers for the completion of a second nucleic acid strand which is substantially complementary to the nucleic acid template; and (d) contacting the products of step (c) with RNA polymerase to generate an RNA library, the library being transcribed from the second nucleic acid strand.

In preferred embodiments, the method is used to introduce one or more mutations into the library; the mixture of substantially complementary single-stranded nucleic acid fragments is generated by cleaving a double-stranded nucleic acid molecule (for example, using DNase I in the presence of $Mn^{2+}$); the mixture of substantially complementary single-stranded nucleic acid fragments is generated by synthesis of random oligonucleotides; the single-stranded nucleic acid template is generated using an M13 phage carrying the nucleic acid, by digestion of one strand of a double-stranded nucleic acid template using gene VI exonuclease or lambda exonuclease (for example, using lambda exonuclease and a double-stranded nucleic acid template having a 5' phosphorylated end), by capture of a biotinylated single nucleic acid strand using streptavidin, or by reverse transcription of RNA; the mixture of substantially complementary single-stranded nucleic acid fragments includes at least about 100 different species of nucleic acid fragments; step (b) is carried out using between 1 and approximately 1000 fragments per single-stranded nucleic acid template; a single strand of the product of step (c) is used as a nucleic acid template and steps (b) and (c) are repeated; steps (b) and (c) are repeated, using, in each round, the product of step (c) as the nucleic acid template; the method further involves providing one or more single-stranded nucleic acid fragments which form a homoduplex with the single-stranded nucleic acid template and carrying out step (b) in the presence of the homoduplex-forming fragments; the promoter is a T7 promoter; the DNA polymerase is T4 DNA polymerase; the DNA polymerase is thermostable (for example, the Taq Stoffel fragment); the DNA ligase is thermostable; the method further involves amplifying the product of step (c) prior to said contacting step (d); the method further involves the step of: (e) translating the RNA library to generate a protein library; the method further involves the step of: (e) linking to the 3' terminus of the coding sequence of each of substantially all of the members of the RNA library an amino acid acceptor molecule; and the method further involves the step of: (f) translating the RNA library to generate an RNA-protein fusion library.

In a second aspect, the invention features a method for reducing sequence variation in a population of nucleic acid molecules, the method involving: (a) providing a first population of single-stranded nucleic acid templates of varying sequence, each of substantially all of the templates including a coding sequence and an operably linked promoter sequence; (b) hybridizing to the members of the first population a second population of substantially complementary single-stranded nucleic acid fragments, the fragments being shorter in length than the nucleic acid template and the fragments being of substantially identical sequence; (c) contacting the hybridization products of step (b) with both a DNA polymerase which lacks strand displacement activity and a DNA ligase under conditions in which the fragments act as primers for the completion of a second nucleic acid strand which is substantially complementary to the nucleic acid template; and (d) contacting the products of step (c) with RNA polymerase to generate a population of RNA molecules, the population of RNA molecules being transcribed from the second nucleic acid strand and having reduced sequence variation relative to the first population of single-stranded nucleic acid templates.

In preferred embodiments, the method is used to remove one or more mutations from the first population of single-stranded nucleic acid templates; step (b) involves hybridization of the first population of single-stranded nucleic acid templates to two or more different populations of substantially complementary single-stranded nucleic acid fragments; the second population of substantially complementary single-stranded nucleic acid fragments is generated by cleaving a double-stranded nucleic acid molecule (for example, using DNase I in the presence of $Mn^{2+}$); the second population of substantially complementary single-stranded nucleic acid fragments is generated by synthesis of random oligonucleotides; the single-stranded nucleic acid template is generated using an M13 phage carrying the nucleic acid, by digestion of one strand of a double-stranded nucleic acid template using gene VI exonuclease or lambda exonuclease (for example, using lambda exonuclease and a double-stranded nucleic acid template having a 5' phosphorylated end), by capture of a biotinylated single nucleic acid strand using streptavidin, or by reverse transcription of RNA; step (b) is carried out using between 1 and approximately 1000 single-stranded nucleic acid fragments per single-stranded nucleic acid template; a single strand of the product of step (c) is used as a nucleic acid template and steps (b) and (c) are repeated; steps (b) and (c) are repeated, using, in each round, the product of step (c) as the nucleic acid template; the promoter is a T7 promoter; the DNA polymerase is T4 DNA polymerase; the DNA polymerase is thermostable (for example, the Taq Stoffel fragment); the DNA ligase is thermostable; the method further involves amplifying the product of step (c) prior to said contacting step (d); the method further involves the step of: (e) translating the population of RNA molecules to generate a protein library; the method further involves the step of: (e) linking to the 3' terminus of the coding sequence of each of substantially all of the members of the population of RNA molecules an amino acid acceptor molecule; and the method further involves the step of: (f) translating the population of RNA molecules to generate an RNA-protein fusion library.

In a third aspect, the invention features a method for generating a nucleic acid library, the method involving: (a) providing a population of single-stranded nucleic acid templates, each of the templates including a coding sequence; (b) providing a population of single-stranded nucleic acid molecules of varying sequence, the population of single-stranded nucleic acid templates and the population of single-stranded nucleic acid molecules of varying sequence being substantially complementary; (c) hybridizing the population of single-stranded nucleic acid templates with the population of single-stranded nucleic acid molecules of varying sequence under conditions sufficient to form duplexes; and (d) contacting the duplexes with one or more excision/repair enzymes under conditions that allow the enzymes to correct mismatched base pairs in the duplexes.

In preferred embodiments, the method further involves providing a population of single-stranded templates derived from the product of step (d) and repeating steps (c) and (d); and the steps (c) and (d) are repeated, using, in each round, a population of single-stranded templates derived from the product of step (d).

In a fourth aspect, the invention features a method for generating a nucleic acid library, the method involving: (a) providing a population of single-stranded nucleic acid templates, each of the templates including a coding sequence; (b) hybridizing to the population of single-stranded nucleic acid templates a mixture of substantially complementary single-stranded nucleic acid fragments, the fragments being shorter in length than the nucleic acid template; (c) contacting each of the hybridization products of step (b) with both a DNA polymerase which lacks strand displacement activity and a DNA ligase under conditions in which the fragments act as primers for the completion of a second nucleic acid strand which is substantially complementary to the nucleic acid template; and (d) contacting the products of step (c) with one or more excision/repair enzymes under conditions that allow the enzymes to correct mismatched base pairs in the products.

In preferred embodiments, the method further involves providing a population of single-stranded templates derived from the product of step (d) and repeating steps (b)–(d); and steps (b)–(d) are repeated, using, in each round, a population of single-stranded templates derived from the product of step (d).

In preferred embodiments of the third and fourth aspects of the invention, the contacting with the excision/repair enzymes is carried out in vivo (for example, in a bacterial cell); the contacting with the excision/repair enzymes is carried out in vitro; the single-stranded nucleic acid template is generated using an M13 phage carrying the nucleic acid, by digestion of one strand of a double-stranded nucleic acid template using gene VI exonuclease or lambda exonuclease (for example, using lambda exonuclease and a double-stranded nucleic acid template having a 5' phosphorylated end), by capture of a biotinylated single nucleic acid strand using streptavidin, or by reverse transcription of RNA; step (b) is carried out using between 1 and approximately 1000 single-stranded nucleic acid molecules of varying sequence or single-stranded nucleic acid fragments per single-stranded nucleic acid template; the method further involves the step of: (e) amplifying the product of step (d); each of the coding sequences is operably linked to a promoter sequence; the method further involves the step of: (e) transcribing the products of step (d) to generate an RNA library; the method further involves the step of: (f) translating the RNA library to generate a protein library; the method further involves the step of: (f) linking to the 3' terminus of the coding sequence of each of substantially all of the members of the RNA library an amino acid acceptor molecule; and the method further involves the step of: (g) translating the RNA library to generate an RNA-protein fusion library.

As used herein, by a "library" is meant at least $10^3$, preferably, at least $10^5$, more preferably, at least $10^8$ or $10^{10}$, yet more preferably, at least $10^{12}$, and, most preferably, at least $10^{14}$ molecules having a nucleic acid and/or an amino acid component.

By a "mixture" of nucleic acid fragments is meant at least 100, preferably, at least 500, more preferably, at least 1000, and, most preferably, at least 1500 nucleic acid fragments.

By a "promoter sequence" is meant any nucleic acid sequence which provides a functional RNA polymerase binding site and which is sufficient to allow transcription of a proximal coding sequence.

By "substantially complementary" is meant that a nucleic acid strand possesses a sufficient number of nucleotides which are capable of forming matched Watson-Crick base pairs with a second nucleic acid strand to produce one or more regions of double-strandedness between the two nucleic acids. It will be understood that each nucleotide in a nucleic acid molecule need not form a matched Watson-Crick base pair with a nucleotide in an opposing strand to be substantially complementary, and that in a "mixture of substantially complementary single-stranded nucleic acid fragments," a significant fraction of the fragments will contain one or more nucleotides which form mismatches with the "single-stranded nucleic acid template."

By "strand displacement activity" is meant the ability of a polymerase or its associated helicase to disrupt base pairing between two nucleic acid strands.

By "mutation" is meant any nucleotide change and includes sequence alterations that result in phenotypic differences as well as changes which are silent.

By "duplex" is meant is meant a structure formed between two annealed nucleic acid strands in which sufficient sequence complementarity exists between the strands to maintain a stable hybridization complex. A duplex may be either a "homoduplex," in which all of the nucleotides in the first strand appropriately base pair with all of the nucleotides in the second opposing strand, or a heteroduplex. By a "heteroduplex" is meant a structure formed between two annealed strands of nucleic acid in which one or more nucleotides in the first strand do not or cannot appropriately base pair with one or more nucleotides in the second opposing complementary strand because of one or more mismatches. Examples of different types of heteroduplexes include those which exhibit an exchange of one or several nucleotides, and insertion or deletion mutations.

By "random oligonucleotides" is meant a mixture of oligonucleotides having sequence variation at one or more nucleotide positions. Random oligonucleotides may be produced using entirely random or partially random synthetic approaches or by intentionally altering an oligonucleotide in a directed fashion.

By an "amino acid acceptor molecule" is meant any molecule capable of being added to the C-terminus of a growing protein chain by the catalytic activity of the ribosomal peptidyl transferase function. Typically, such molecules contain (i) a nucleotide or nucleotide-like moiety (for example, adenosine or an adenosine analog (di-methylation at the N-6 amino position is acceptable)), (ii) an amino acid or amino acid-like moiety (for example, any of the 20 D- or L-amino acids or any amino acid analog thereof (for example, O-methyl tyrosine or any of the analogs described by Ellman et al., Meth. Enzymol. 202:301, 1991)), and (iii) a linkage between the two (for example, an ester, amide, or ketone linkage at the 3' position or, less preferably, the 2' position); preferably, this linkage does not significantly perturb the pucker of the ring from the natural ribonucleotide conformation. Amino acid acceptors may also possess a nucleophile, which may be, without limitation, an amino group, a hydroxyl group, or a sulfhydryl group. In addition, amino acid acceptors may be composed of nucleotide mimetics, amino acid mimetics, or mimetics of a combined nucleotide-amino acid structure.

By an amino acid acceptor being linked "to the 3' terminus" of a coding sequence is meant that the amino acid acceptor molecule is positioned after the final codon of that coding sequence. This term includes, without limitation, an amino acid acceptor molecule that is positioned precisely at the 3' end of the coding sequence as well as one which is separated from the final codon by intervening coding or non-coding sequence (for example, a sequence corresponding to a pause site). This term also includes constructs in which coding or non-coding sequences follow (that is, are 3' to) the amino acid acceptor molecule. In addition, this term encompasses, without limitation, an amino acid acceptor molecule that is covalently bonded (either directly or indirectly through intervening nucleic acid sequence) to the coding sequence, as well as one that is joined to the coding sequence by some non-covalent means, for example, through hybridization using a second nucleic acid sequence that binds at or near the 3' end of the coding sequence and that itself is bound to an amino acid acceptor molecule.

By an "RNA-protein" fusion is meant any molecule that includes a ribonucleic acid covalently bonded through an amide bond to a protein. This covalent bond is resistant to cleavage by a ribosome.

By a "protein" is meant any two or more naturally occurring or modified amino acids joined by one or more peptide bonds. "Protein," "peptide," and "polypeptide" are used interchangeably herein.

By "a population of single-stranded templates of varying sequence" is meant that the nucleic acid species of the population possess sequences which differ at one or more nucleotide positions.

By "excision/repair enzymes" is meant any combination of enzymes sufficient to replace a mismatched base pair or loop with a standard base pair (i.e., A:T or G:C).

BRIEF DESCRIPTION OF THE DRAWINGS

FIGS. 3, 4-1, 4-2, 5-1, and 5-2 are schematic representations of exemplary template-mediated fragment recombination methods.

DETAILED DESCRIPTION

The present invention involves a number of novel and related methods for the random recombination of nucleic acid sequences, facilitating the generation of DNA, RNA, and protein libraries into which genetic alterations have been introduced. As described in more detail below, in one preferred embodiment, this technique is carried out in vitro and is used to generate traditional protein libraries or RNA-protein fusion libraries, either of which may then be used in combination with any of a variety of methods for the selection of desired proteins or peptides (or their corresponding coding sequences) from library populations. This general approach provides a means for the introduction of mutations into protein libraries in an unbiased fashion and also provides a technique by which unfavorable mutations may be removed from a library or selected pool, or "backcrossed" out of a population of molecules during subsequent rounds of selection.

Fragment Recombination

Figure 1:
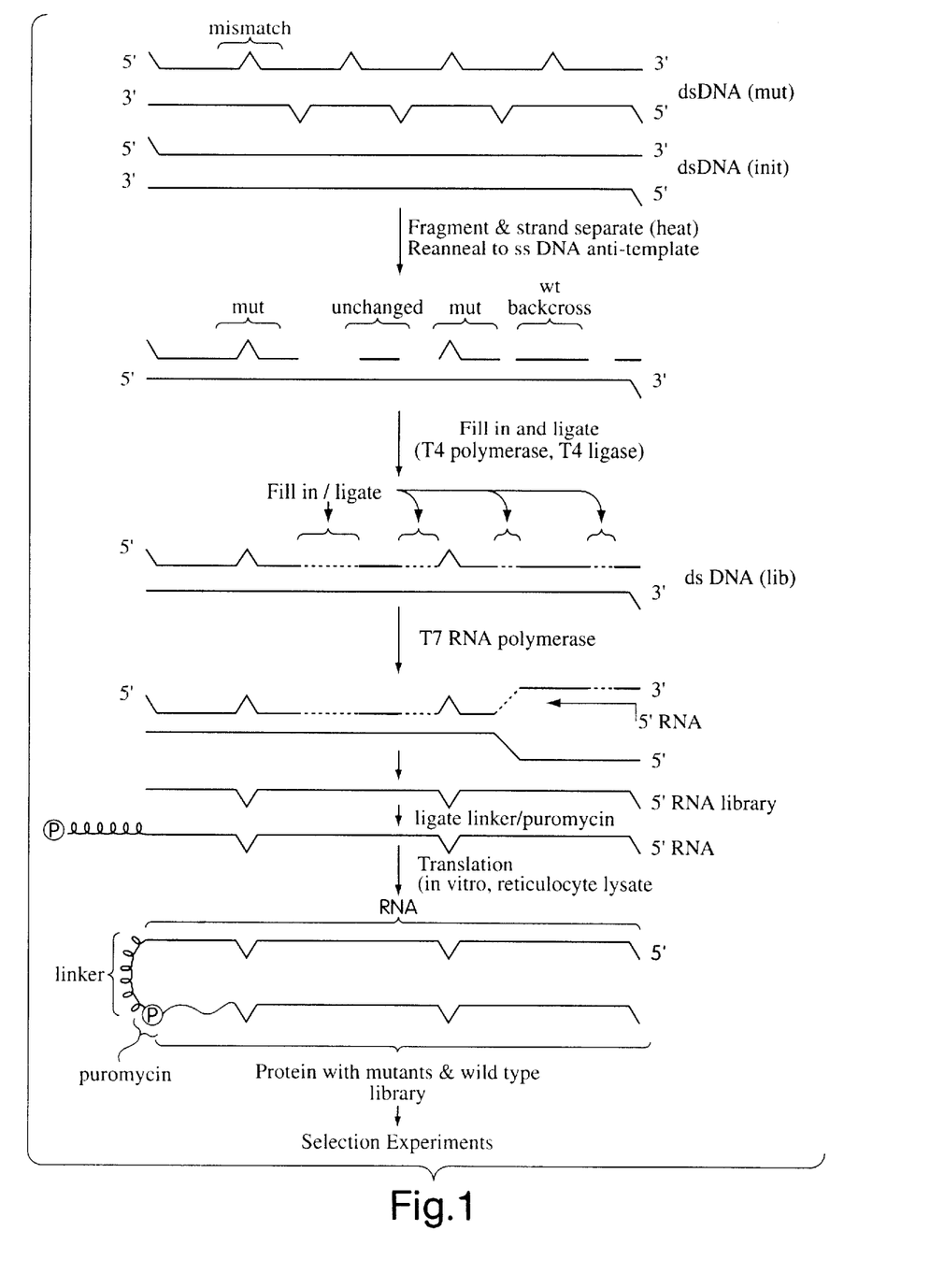
FIG. 1 is a schematic representation of an exemplary fragment recombination method for generating highly diverse RNA-protein fusion libraries. In this method, the fragments are derived from a double-stranded DNA molecule into which sequence variation is introduced.

According to one preferred method of the invention, a library is generated by the production of mutant fragments and the random recombination of these fragments with an unmutated (typically, wild-type) sequence. One example of this general approach is shown in FIG. 1. As indicated in this figure, mutations are first randomly introduced into an initial double-stranded DNA sequence (termed "dsDNA(init)"). This produces a population of mutant double-stranded DNA sequences, which, in FIG. 1, is termed "dsDNA(mut)." These mutations may be introduced by any technique, including PCR mutagenesis (which relies on the poor error-proofing mechanism of Taq polymerase), site-directed mutagenesis, or template-directed mutagenesis (for example, as described in Joyce and Inoue, Nucl. Acids Res. 17:171, 1989. The DNA in this mutation-containing population is subsequently fragmented using any of a variety of standard methods. For example, the DNA may be partially degraded using one or more nucleases (such as DNase I, micrococcal nuclease, restriction endonucleases, or P1 nuclease), or may be fragmented chemically using, for example, Fe.EDTA. Alternatively, mutation-containing fragments may be generated by limited nucleotide consumption during polymerization (for example, during PCR amplification), or by simple physical shearing (for example, by sonication). Preferable fragment sizes range from 25–1000 base pairs and are most preferably in the range of 50–150 base pairs.

The DNA fragments are then heated and subsequently annealed to a full-length single-stranded DNA template which is identical to the initial DNA in sequence and which is the non-coding (or minus) strand of that DNA. In addition, in this hybridization mixture is included a second type of fragment, sometimes referred to as a "terminator fragment" (Joyce and Inoue, Nucl. Acids Res. 17:171, 1989). This terminator fragment is complementary to the 3' end of the single-stranded template and provides a polymerization primer which binds to the template in a manner that is relatively independent of the number or nature of the randomly annealed, mutation-containing fragments.

Single-stranded templates may be generated by any standard technique, for example, by using an M13 phage carrying the DNA sequence, by digestion of the coding strand of a dsDNA(init) molecule using gene VI exonuclease (Nikiforov et al, PCR Methods Appl. 3:285, 1994) or lambda exonuclease (Higuchi and Ochman, Nucl. Acids Res 17: 5865, 1989), by capture of a biotinylated DNA strand using immobilized streptavidin (Joyce and Inoue, Nucl. Acids Res. 17:171, 1989), or by reverse transcription of RNA. To carry out the template-fragment hybridization, templates are mixed with fragments using no less than one fragment molecule per template molecule and no more than approximately 1000 fragment molecules per template molecule. A low ratio of fragments to templates produces progeny strands that closely resemble the templates, whereas a higher ratio produces progeny that more closely resemble the fragments. Hybridization conditions are determined by standard methods and are designed to allow for the formation of heteroduplexes between the template and the fragments. Exemplary hybridization techniques are described, for example, in Stemmer. U.S. Pat. No. 5,605,793.

Once annealed to the template, the fragments are joined together by treating with both a DNA polymerase that lacks strand displacement activity and a DNA ligase. DNA polymerases useful for this purpose include, without limitation, T4 DNA polymerase and reconstituted DNA pol II from *E. coli* (see, for example, Hughes et al., J. Biol. Chem. 266:4568, 1991). Any DNA ligase (for example, T4 DNA ligase) may be utilized. In this step, the DNA duplexes may be treated first with the DNA polymerase and then with the DNA ligase, or with both enzymes simultaneously, and the step may be carried out, for example, as described in Joyce and Inoue (Nucl. Acids Res. 17:711, 1989). As shown in FIG. 1, this step generates a population of double-stranded DNAs (termed "dsDNA(lib)), each member of which includes one strand typically having one or more introduced mutations. Because both the mutations initially introduced and the number and nature of the fragments annealed are random, different duplexes in the population contain different mutant sequences.

Figure 2:
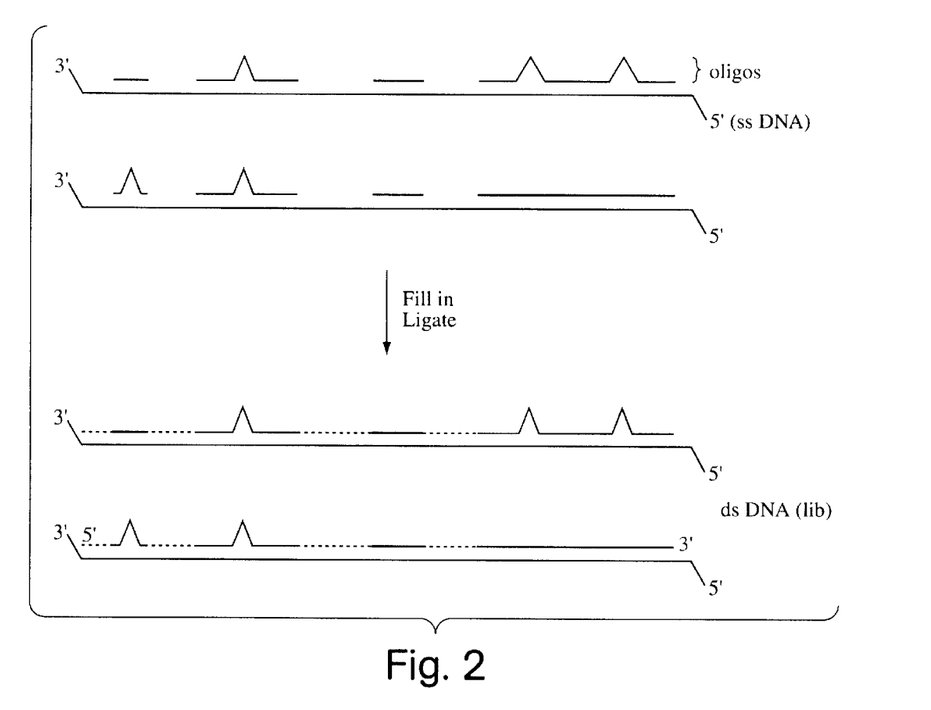
FIG. 2 is a schematic representation of the initial steps of a second exemplary fragment recombination method. In this method, the fragments are synthetic oligonucleotides into which sequence variation is introduced.

An alternative to this general approach for generating a double-stranded DNA library is shown in FIG. 2. By this alternative approach, single-stranded oligonucleotide fragments are synthesized which correspond to portions of the coding strand of an initial double-stranded DNA molecule. These oligonucleotide fragments preferably range from 5–2000 nucleotides, and most preferably range from 20–100 nucleotides in length and are generated, for example, using any standard technique of nucleic acid synthesis. These oligonucleotides may be synthesized with completely random or semi-random mutations by any standard technique. Preferably, such oligonucleotides include up to 3 introduced mismatches per 20 nucleotide segment and are devoid of in frame stop codons. In addition, in certain cases, it may be desirable or necessary to increase the hybridization potential of the oligonucleotide through the introduction of non-natural, affinity-enhancing base pairs, such as C-5 propyne uridine or C-5 propyne cytidine. These techniques are described, for example, in Wagner et al., Science 25 260:1510, 1993.

These mutation-containing oligonucleotide fragments are next annealed to single-stranded templates which, as above, are full-length strands identical in sequence to the non-coding (or minus) strand of the initial DNA. The fragments are joined together using DNA polymerase and DNA ligase, also as described above, to create a double-stranded DNA library (dsDNA(lib)). Again, this library contains a population of duplex molecules, containing an array of different coding strands having mutations which differ in number, position, and identity.

If desired, the above steps may be repeated, for either the fragment or the oligonucleotide approach, to introduce varying numbers of mutations into a DNA molecule. In particular, the mutated strands become the initial single-stranded templates, and mutant fragments or oligonucleotides are annealed to those strands and polymerized and ligated.

In one exemplary procedure, this template-mediated fragment recombination procedure may be carried out using both a thermostable polymerase (for example, the Taq Stoffel fragment) and a thermostable ligase, and the DNA fragments may be generated by DNase I digestion in the presence of $Mn^{2+}$.

Figure 3:
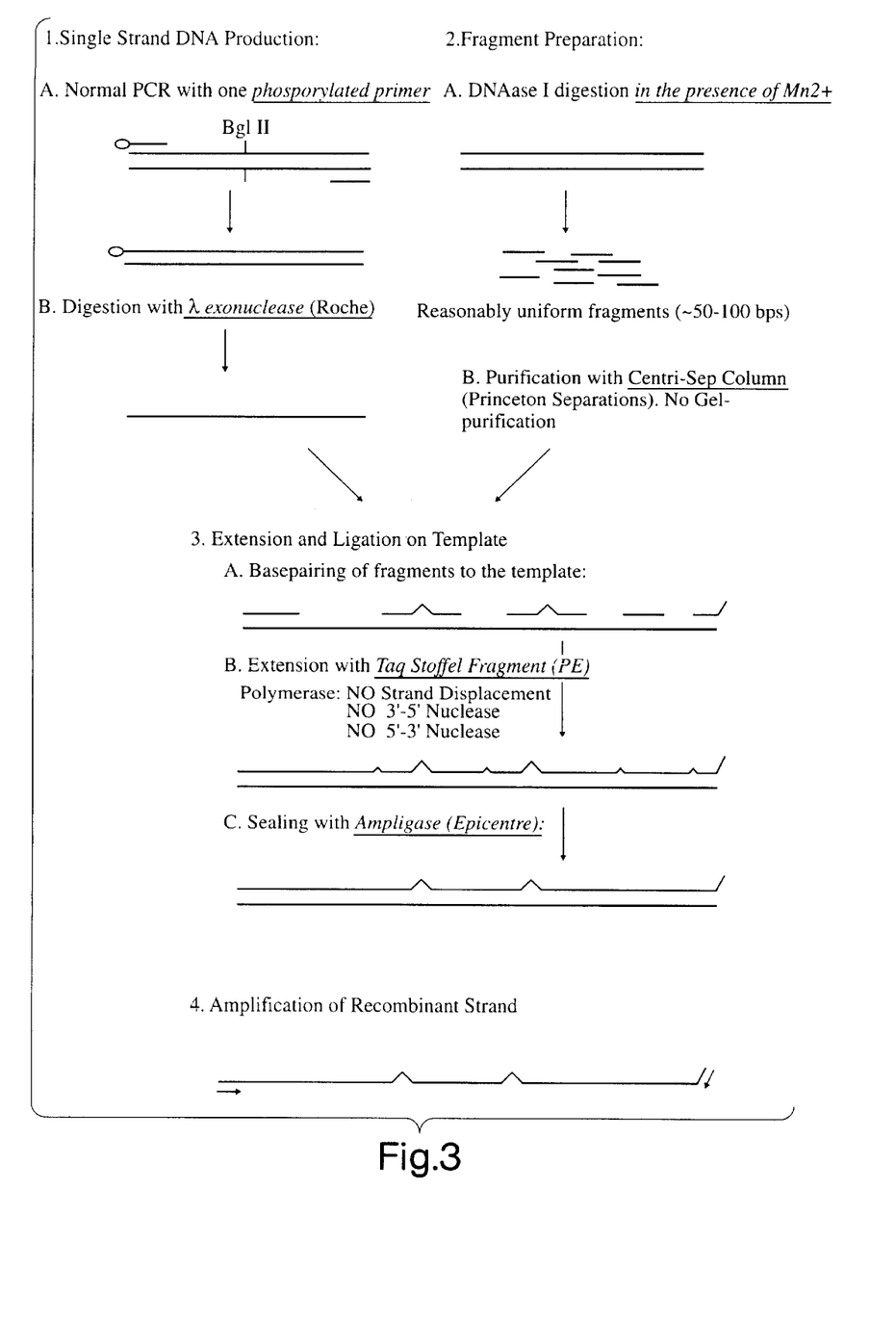

In particular, this technique, which is shown in FIG. 3, was carried out as follows. Single-stranded DNA was obtained using lambda exonuclease (Roche Biochemicals, Indianapolis, Ind.), which digests one strand of a DNA duplex from a 5' phosphorylated end (Ausubel et al., *Current Protocols in Molecular Biology*, Wiley Press, New York, N.Y.). The initial duplex DNA was prepared by standard PCR amplification using two primers, one of which was phosphorylated at the 5' end (Ausubel et al., supra). When digested, a small fraction of duplex DNA (about 20–30%) remained intact, presumably due to incomplete primer phosphorylation. To monitor recombination events, the template DNA included a unique Bgl II site in the middle of the sequence. This site was absent in the DNA used for fragment preparation.

DNA fragments were produced by digestion with DNase I (Roche Biochemicals, Indianapolis, Ind.) in the presence of 10 mM $Mn^{2+}$ at 15° C. for 4 minutes, followed by addition of EDTA to quench the reaction (Lorimer et al., Nucl. Acids Res. 23: 3067–3068, 1995). The fragments were then purified using a Centri-Sep column (Princeton Separations, Adelphia, N.J.). The presence of $Mn^{2+}$ improved the digestion reaction and produced digestion products that were uniform in size (about 5–100 bp). This is advantageous because the presence of small amounts of intact fragments can interfere with amplification of the recombinant strand and also because smaller fragments facilitate recombination events.

Following hybridization of the fragments to the template strand, DNA polymerase Taq Stoffel fragment (PE Applied Biosystems, Foster City, Calif.) and the thermolabile DNA ligase, Ampligase (Epicentre Technologies, Madison, Wis.) were added to fill in the regions between the fragments and seal the gaps. The Taq Stoffel fragment was well-suited for template-directed fragment recombination for a number of reasons. First, it was as active as the full-length Taq polymerase, and like Taq it lacked both 3'–5' exonuclease activity and strand displacement activity. Moreover, Taq Stoffel fragment was also devoid of 5'–3' exonuclease activity, preventing the polymerase from either degrading input DNA (i.e., template or fragment DNA) or displacing or degrading DNA fragments that it encountered during the filling-in reactions, improving recombination frequencies. The thermostable ligase was similarly advantageous; this ligase was stable and highly active at 42–65° C. The use of both a thermostable polymerase and ligase allowed or filling-in reactions to be carried out at higher temperatures, reducing the interference from localized secondary structures of single-stranded DNAs. In addition, the Taq Stoffel fragment permitted filling reactions to proceed at higher rates and with greater processivity.

Recombination reaction mixtures were incubated at 50° C. for 2 minutes, 65° C. for 15 minutes, and finally at 50° C. for 20 minutes. The nominal ratio of template DNA to fragment was 1:1 (as determined before digestion with nuclease or DNase I). The mixtures were then treated with an S-400 HR column (Pharmacia, Piscataway, N.J.) to remove any remaining DNA fragments.

The recombinant strand was then amplified by PCR. To allow for amplification, an external oligonucleotide primer was added during the recombination reaction. As shown in FIG. 3, this primer contained a 5' region that was complementary to the template, while the 3'-end served as a handle for the amplification reaction of the recombinant strand by PCR.

Bgl II digestion experiments revealed that about 10% of the recombinant products lacked Bgl II sites, demonstrating that recombination had taken place. Control reactions with fragment DNA alone produced no significantly visible product.

Control reactions with template DNA alone also produced products having Bgl II sites, presumably due to amplification of the template DNA alone. To reduce such background product, single-stranded DNA may be produced by conversion of the double-stranded template DNA into mRNA, followed by reverse transcription of the mRNA to synthesize pure, single-stranded material. The mRNA is then selectively removed by digestion with RNaseH (as shown in FIGS. 4 and 5, step 1). This approach eliminates possible interference with residual double-stranded template DNA.

Figure 41:
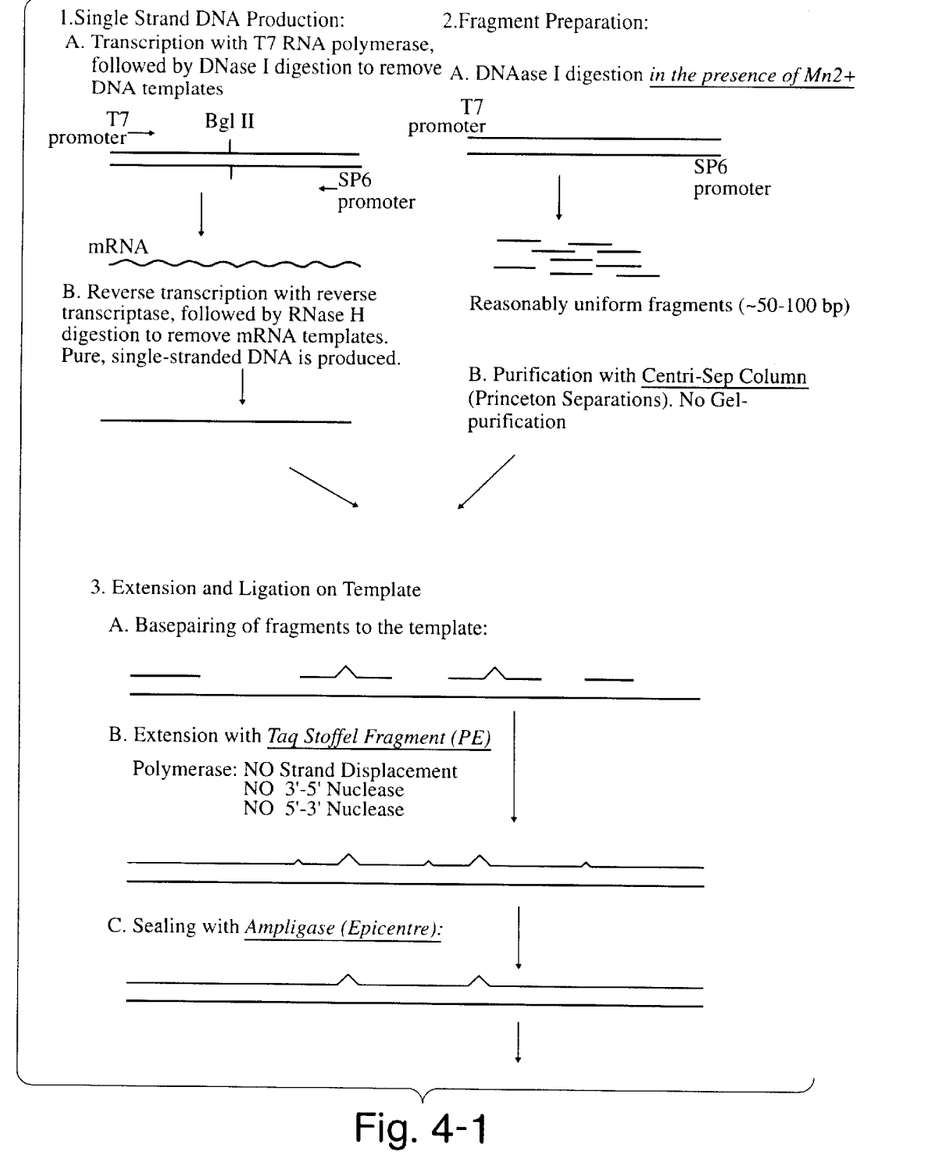
Figure 42:
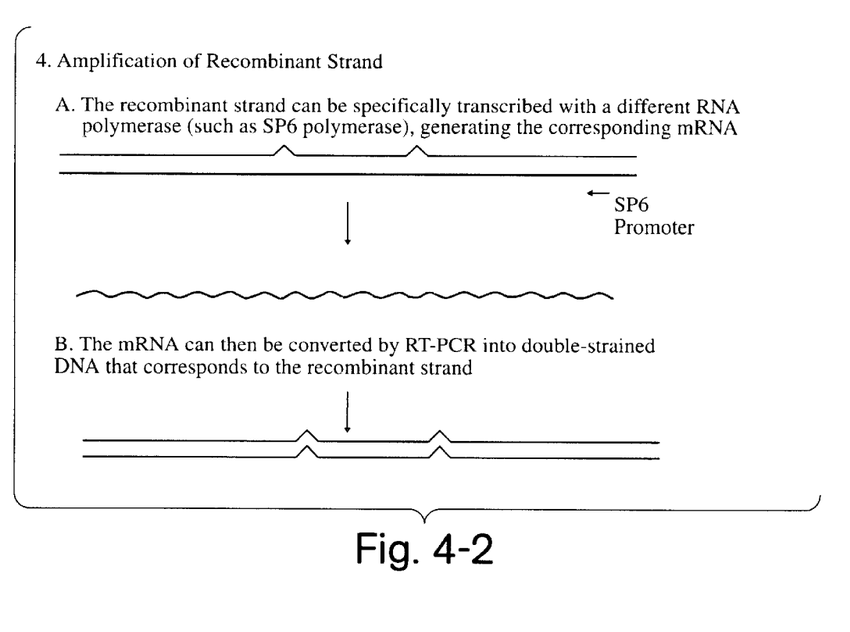

In addition, to improve selectivity during recombinant strand amplification, a second RNA promoter region may be incorporated into the sequences for both the template and fragment DNAs. As shown in FIG. 4, one exemplary promoter for this purpose is the SP6 promoter. Upon completion of the recombination reaction, the recombinant strand is selectively transcribed into mRNA using SP6 polymerase, and then converted into double-stranded DNA, for example, by standard RT-PCR.

Figure 51:
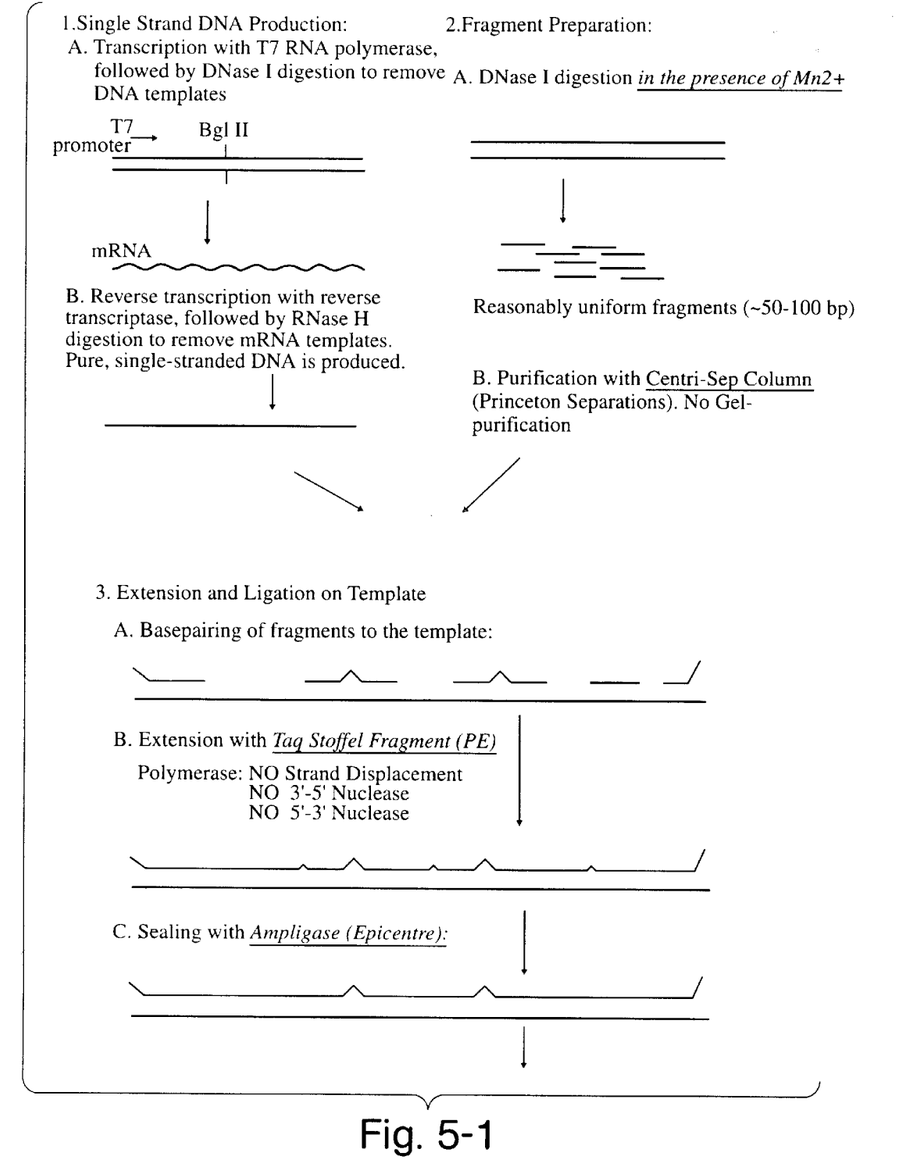
Figure 52:
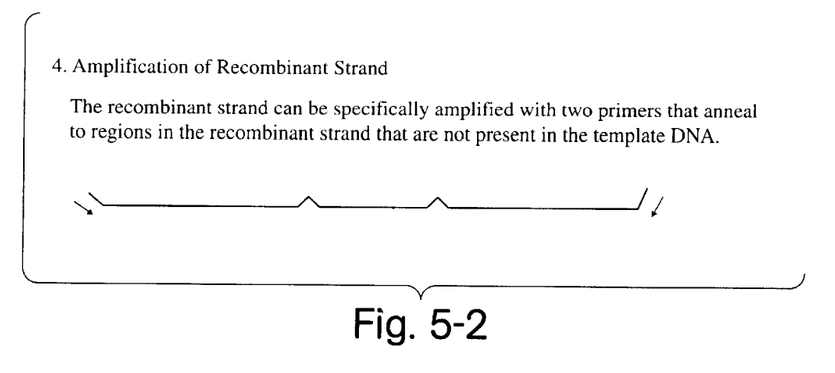

Alternatively, as shown in FIG. 5, two short oligonucleotides may be incorporated into the fragment DNA such that mismatched regions are created at both ends of the template upon annealing of fragments (FIG. 5, step 3). Following the recombination reaction, the recombinant strand is selectively amplified using two primers that anneal to these mismatched regions, neither of which is present in the template DNA.

Methods for Backcrossing

As generally described above, the methods of the invention are used to introduce mutations into an initial DNA sequence. In addition, these techniques may be used to remove or reduce in frequency undesirable mutations from a DNA library. According to this approach, following fragmentation of the dsDNA(mut), oligonucleotides of wild-type sequence or specific fragments of unmutated or wild-type DNA (wtDNA) may be added to the single-stranded template together with the dsDNA(mut) fragments or oligonucleotides. The fragments are strand-separated (if necessary), annealed to the full-length single-stranded template, and joined together using DNA polymerase and DNA ligase, as described above. The use of a high concentration of unmutated oligonucleotide or fragment, relative to the corresponding mutant fragment, allows for the generation of libraries in which undesirable mutations are minimized or eliminated.

In addition, this approach may be used with existing mutation-containing libraries to similarly decrease or eliminate undesirable sequences. This approach involves an initial library having mutant sequences and the annealing, polymerization, and ligation of fragments or oligonucleotides of wild-type sequence, as generally described above.

RNA, Protein and RNA-Protein Libraries

In one preferred embodiment of the invention, the DNA libraries described above further include an RNA polymerase binding site, for example, for T7 or SP6 polymerase. Such binding sites are described, for example, in Milligan et al., Proc. Natl. Acad. Sci. USA 87:696, 1990. This site is positioned upstream of the coding sequence at a location which allows for transcription of the sequence. Typically such sites are located at between 5–2000 base pairs upstream of the coding sequence.

Libraries containing RNA polymerase binding sites may be altered as described above. Following polymerization and ligation, the dsDNA(lib) may be transcribed directly, for example, using an in vitro transcription system, to generate an RNA library. Alternatively, the dsDNA(lib) may be transcribed and translated directly, for example, using in vitro transcription and translation systems, to generate a protein library. Exemplary in vitro transcription systems and in vitro translation systems include T7 transcription systems, and rabbit reticulocyte, wheat germ, yeast, and *E. coli* translation systems.

If desired, the number of copies of each RNA or protein in the library may be increased by including a strand-specific amplification step prior to transcription. For example, PCR amplification may be carried out by incorporating unique primer-binding sequences into the mutant strand during the polymerization and ligation steps. These sequences may be incorporated as either mismatches or sequence extensions at one or both ends of the DNA, allowing amplification of the newly-synthesized strand without amplification of the template strand. Alternatively, linear amplification can be achieved by multiple cycles of annealing and extension of a single oligonucleotide primer that is complementary to the 3' end of the newly-synthesized strand. Subsequent PCR and transcription steps produce a majority of RNA corresponding to mutant sequences with only a small proportion of template-derived sequences.

In one preferred approach, the above methods for introducing mutations or for backcrossing out undesirable mutations may be used to produce highly diverse RNA-protein libraries. Such libraries may be constructed by ligating linkers containing a non-hydrolyzable amino acid acceptor molecule, such as puromycin, to the 3' termini of the RNAs in a library (for example, produced as described above). Exemplary techniques for generating RNA-protein fusions are described, for example, in Szostak et al., U.S. Ser. No. 09/007,005; and Roberts et al., Proc. Natl. Acad. Sci. USA 94:12297, 1997. Subsequent translation of these RNAs generates a library of RNA-protein fusion molecules that may subsequently be used in in vitro selection experiments.

In addition, if desired, RNA or RNA-protein fusion molecules, once selected, may be used as templates in standard PCR reactions to obtain the corresponding coding sequence. Thus, this method provides a means for carrying out fragment recombination, molecular backcrossing, selection of proteins and/or peptides, and selection of their corresponding coding sequences, all in an in vitro system.

Excision/Repair

In addition to fragment recombination approaches, excision/repair may also be used to alter library sequences. This approach may be used to generate DNA, RNA, and RNA-protein fusion libraries. This technique relies on the fact that the dsDNA(lib)s, produced by any of the methods described above, by their nature, contain a certain number of mismatched base pairs. To generate diversity in the library sequences, these mismatches are repaired in vitro by excision/repair enzymes. This may be carried out using any excision repair system (for example, as described in Jaiswal et al., Nucl. Acids Res. 26:2184, 1998; or Fortini et al., Biochemistry 11:3575, 1998.)

Alternatively, the excision/repair step may be carried out by transforming a dsDNA(lib) into a bacterial or yeast strain and exploiting the bacterial or yeast repair systems in vivo. Again, this step may be carried out by transforming the library into any standard in vivo excision/repair system. Exemplary systems are described, without limitation, in Campbell et al., Mutat. Res. 211:181, 1989; Bishop and Kolodner, Mol. Cell Biol. 6:3401, 1986; Fishel et al., J. Mol. Biol. 188:147, 1986; and Westmoreland et al., Genetics 145:29, 1997.

Because the above repair processes are random, this excision/repair method sometimes results in the introduction of mutations into a library sequence and at other times results in the backcrossing of wild-type sequence alterations into the coding strand.

In an alternative to the above approaches, in vitro or in vivo excision/repair may also be used directly to generate diverse libraries using as a substrate a mixture of dsDNA (mut) (for example, produced as described above) and dsDNA(init) or wtDNA. In this technique, the mixture is strand-separated and reannealed, and is then either incubated in vitro with excision/repair enzymes or transformed into bacteria to utilize the bacterial excision/repair system (for example, as described above). In this manner, mutations may be randomly introduced into a sequence, and wild-type sequences may be backcrossed into dsDNA(mut) molecules.

What is claimed is:

1. A method for generating a nucleic acid library, said method comprising:
   (a) providing a population of single-stranded nucleic acid templates, each of said templates comprising a coding sequence and an operably linked promoter sequence;
   (b) hybridizing to said population of single-stranded nucleic acid templates a mixture of substantially complementary single-stranded nucleic acid fragments, said fragments being shorter in length than said nucleic acid templates;
   (c) contacting each of the hybridization products of step (b) with both a DNA polymerase which lacks strand displacement activity and a DNA ligase, under conditions in which said fragments act as primers for the completion of second nucleic acid strands which are substantially complementary to said nucleic acid templates; and
   (d) contacting the products of step (c) with RNA polymerase to generate an RNA library, said library being transcribed from said second nucleic acid strands.

2. The method of claim 1, wherein said method is used to introduce one or more mutations into said library.

3. The method of claim 1, wherein said mixture of substantially complementary single-stranded nucleic acid fragments is generated by cleaving double-stranded nucleic acid molecules.

4. The method of claim 3, wherein said cleaving is carried out using DNase I in the presence of $Mn^{2+}$.

5. The method of claim 1, wherein said mixture of substantially complementary single-stranded nucleic acid fragments is generated by synthesis of random oligonucleotides.

6. The method of claim 1, wherein said single-stranded nucleic acid templates are generated by using an M13 phage carrying said nucleic acid templates, by digestion of one strand of double-stranded nucleic acid molecules using gene VI exonuclease or lambda exonuclease, by capture of biotinylated single nucleic acid strands using streptavidin, or by reverse transcription of RNA.

7. The method of claim 6, wherein said single-stranded nucleic acid templates are generated using lambda exonuclease and double-stranded nucleic acid molecules comprising a 5' phosphorylated end.

8. The method of claim 1, wherein said mixture of substantially complementary single-stranded nucleic acid fragments comprises at least about 100 different species of nucleic acid fragments.

9. The method of claim 1, wherein step (b) is carried out using between 1 and approximately 1000 fragments per each of said single-stranded nucleic acid templates.

10. The method of claim 1, further comprising generating complementary strands from said second nucleic acid strands, providing said complementary strands as said population of single-stranded nucleic acid templates, and repeating steps (b) and (c) for one or more rounds and then repeating step (d).

11. The method of claim 1, wherein said method further comprises providing one or more single-stranded nucleic acid fragments which form a homoduplex with said single-stranded nucleic acid templates and carrying out step (b) in the presence of said homoduplex-forming fragments.

12. The method of claim 1, wherein said promoter is a T7 promoter.

13. The method of claim 1, wherein said DNA polymerase is T4 DNA polymerase.

14. The method of claim 1, wherein said DNA polymerase is thermostable.

15. The method of claim 14, wherein said DNA polymerase is Taq Stoffel fragment.

16. The method of claim 1, wherein said DNA ligase is thermostable.

17. The method of claim 1, wherein said method further comprises amplifying said product of step (c) prior to said contacting step (d).

18. The method of claim 1, wherein said method further comprises the step of:
   (e) translating said RNA library to generate a protein library.

19. The method of claim 1, wherein said method further comprises the step of:
   (e) linking to the 3' terminus of said coding sequence of each of substantially all of the members of said RNA library an amino acid acceptor molecule.

20. The method of claim 19, wherein said method further comprises the step of:
   (f) translating said RNA library to generate an RNA-protein fusion library.

21. A method for reducing sequence variation in a population of nucleic acid molecules, said method comprising:
   (a) providing a first population of single-stranded nucleic acid templates of varying sequence, each of substantially all of said templates comprising a coding sequence and an operably linked promoter sequence;
   (b) hybridizing the members of said first population of single-stranded nucleic acid templates to a second population of single-stranded nucleic acid fragments, said fragments being shorter in length than said nucleic acid templates and said fragments being substantially complementary to said nucleic acid templates, wherein a subpopulation of said second population of single-stranded nucleic acid fragments comprises a substantially identical sequence and hybridizes to a region of varying sequence;

(c) contacting the hybridization products of step (b) with both a DNA polymerase which lacks strand displacement activity and a DNA ligase under conditions in which said fragments act as primers for the completion of second nucleic acid strands which are substantially complementary to said nucleic acid templates; and (d) contacting the products of step (c) with RNA polymerase to generate a third population of RNA molecules, said third population of RNA molecules being transcribed from said second nucleic acid strands and said third population of RNA molecules having reduced sequence variation relative to said first population of single-stranded nucleic acid templates.

22. The method of claim 21, wherein said fragments are of wildtype or unmutated sequence.

23. The method of claim 21, wherein said method is used to remove one or more mutations from said first population of single-stranded nucleic acid templates.

24. The method of claim 21, wherein said second population of single-stranded nucleic acid fragments comprises two or more different subpopulations of single-stranded nucleic acid fragments that are substantially complementary to said first population.

25. The method of claim 21, wherein said second population of substantially complementary single-stranded nucleic acid fragments is generated by cleaving double-stranded nucleic acid molecules.

26. The method of claim 25, wherein said cleaving is carried out using DNase I in the presence of $Mn^{2+}$.

27. The method of claim 21, wherein said second population of substantially complementary single-stranded nucleic acid fragments is generated by synthesis of random oligonucleotides.

28. The method of claim 21, wherein said single-stranded nucleic acid templates are generated by using an M13 phage carrying said nucleic acid templates, by digestion of one strand of double-stranded nucleic acid molecules using gene VI exonuclease or lambda exonuclease, by capture of biotinylated single nucleic acid strands using streptavidin, or by reverse transcription of RNA.

29. The method of claim 28, wherein said single-stranded nucleic acid templates are generated using lambda exonuclease and double-stranded nucleic acid molecules comprising a 5' phosphorylated end.

30. The method of claim 21, wherein step (b) is carried out using between 1 and approximately 1000 single-stranded nucleic acid fragments per each of said single-stranded nucleic acid templates.

31. The method of claim 21, further comprising generating complementary strands from said second nucleic acid strands providing said complementary strands as said first population of single-stranded nucleic acid templates, and repeating steps (b) and (c) for one or more rounds, and then repeating step (d).

32. The method of claim 21, wherein said promoter is a T7 promoter.

33. The method of claim 21, wherein said DNA polymerase is T4 DNA polymerase.

34. The method of claim 21, wherein said DNA polymerase is thermostable.

35. The method of claim 34, wherein said DNA polymerase is Taq Stoffel fragment.

36. The method of claim 21, wherein said DNA ligase is thermostable.

37. The method of claim 21, wherein said method further comprises amplifying said product of step (c) prior to said contacting step (d).

38. The method of claim 21, wherein said method further comprises the step of:

(e) translating said third population of RNA molecules to generate a protein library.

39. The method of claim 21, wherein said method further comprises the step of:

(e) linking to the 3' terminus of said coding sequence of each of substantially all of the members of said third population of RNA molecules an amino acid acceptor molecule.

40. The method of claim 39, wherein said method further comprises the step of:

(f) translating said third population of RNA molecules to generate an RNA-protein fusion library.

41. A method for generating a nucleic acid library, said method comprising:

(a) providing a population of single-stranded nucleic acid templates, each of said templates comprising a coding sequence;

(b) providing a mixture of single-stranded nucleic acid molecules of varying sequence, said population of single-stranded nucleic acid templates and said mixture of single-stranded nucleic acid molecules of varying sequence being substantially complementary;

(c) hybridizing said population of single-stranded nucleic acid templates with said mixture of single-stranded nucleic acid molecules of varying sequence under conditions sufficient to form duplexes;

(d) contacting said duplexes with one or more excision/repair enzymes under conditions that allow said enzymes to replace mismatched base pairs with standard base pairs in said duplexes;

(e) providing a new population of single-stranded nucleic acid templates comprising a coding sequence, said new population of templates being derived from the product of step (d); and (f) substituting said new population of templates for said population of single-stranded nucleic acid templates and repeating steps (b), (c) and (d) for one or more rounds, thereby generating a nucleic acid library.

42. A method for generating a nucleic acid library, said method comprising:

(a) providing a population of single-stranded nucleic acid templates, each of said templates comprising a coding sequence;

(b) hybridizing to said population of single-stranded nucleic acid templates a mixture of substantially complementary single-stranded nucleic acid fragments, said fragments being shorter in length than said nucleic acid templates;

(c) contacting each of the hybridization products of step (b) with both a DNA polymerase which lacks strand displacement activity and a DNA ligase under conditions in which said fragments act as primers for the completion of a second nucleic acid strand which is substantially complementary to said nucleic acid templates; and (d) contacting the products of step (c) with one or more excision/repair enzymes under conditions that allow said enzymes to correct mismatched base pairs in said products, thereby generating a nucleic acid library.

43. The method of claim 42, wherein said method further comprises the steps of:

providing a new population of single-stranded nucleic acid templates comprising coding sequences, said new population of templates being derived from the product of step (d), substituting said new population of templates for said population of single-stranded nucleic acid templates, and repeating steps (b)–(d) for one or more rounds, thereby generating a nucleic acid library.

44. The method of claim 41 or 42, wherein said contacting with said excision/repair enzymes is carried out in a bacterial cell.

45. The method of claim 44, wherein said contacting with said excision/repair enzymes is carried out in a bacterial cell.

46. The method of claim 41 or 42, wherein said contacting with said excision/repair enzymes is carried out in vitro.

47. The method of claim 41 or 42, wherein said single-stranded nucleic acid templates are generated by using an M13 phage carrying said nucleic acid templates, by digestion of one strand of double-stranded nucleic acid templates using gene VI exonuclease or lambda exonuclease, by capture of biotinylated single nucleic acid strands using streptavidin, or by reverse transcription of RNA.

48. The method of claim 47, wherein said single-stranded nucleic acid templates are generated by using lambda exonuclease and double-stranded nucleic acid templates comprising a 5' phosphorylated end.

49. The method of claim 41 or 42, wherein step (b) is carried out using between 1 and approximately 1000 single-stranded nucleic acid molecules of varying sequence or single-stranded nucleic acid fragments per each of said single-stranded nucleic acid templates.

50. The method of claim 41 or 42, wherein said method further comprises the step of:
 (e) amplifying said product of step (d).

51. The method of claim 41 or 42, wherein each of said coding sequences is operably linked to a promoter sequence.

52. The method of claim 51, wherein said method further comprises the step of:
 (e) transcribing the products of step (d) to generate an RNA library.

53. The method of claim 52, wherein said method further comprises the step of:
 (f) translating said RNA library to generate a protein library.

54. The method of claim 52, wherein said method further comprises the step of:
 (f) linking to the 3' terminus of said coding sequence of each of substantially all of the members of said RNA library an amino acid acceptor molecule.

55. The method of claim 54, wherein said method further comprises the step of:
 (g) translating said RNA library to generate an RNA-protein fusion library.

* * * * *